United States Patent [19]

Miyasaka et al.

[11] Patent Number: 5,053,225

[45] Date of Patent: Oct. 1, 1991

[54] FUNCTIONAL ORGANIC THIN FILM CHEMICALLY BONDED TO BIOLOGICALLY ACTIVE AGENT

[75] Inventors: Tsutomu Miyasaka; Yukio Maekawa, both of Kanagawa, Japan

[73] Assignee: Fuji Photo Film Co., Ltd., Kanagawa, Japan

[21] Appl. No.: 325,797

[22] Filed: Mar. 20, 1989

[30] Foreign Application Priority Data

Mar. 18, 1988 [JP] Japan .................................. 63-64968

[51] Int. Cl.$^5$ ...................... A61K 39/00; A61K 37/48
[52] U.S. Cl. ..................................... 424/85.8; 424/88; 424/94.1
[58] Field of Search ................ 525/54.1; 424/78, 85.8, 424/88, 94.1

[56] References Cited

U.S. PATENT DOCUMENTS

| | | | |
|---|---|---|---|
| 3,335,167 | 8/1967 | Tesodo et al. | 525/54.1 |
| 4,161,407 | 7/1979 | Campbell | 525/54.1 |
| 4,294,921 | 10/1981 | Yamaguchi et al. | 525/54.1 |
| 4,687,808 | 8/1987 | Jarrett et al. | 525/54.1 |
| 9,775,714 | 10/1988 | Hermann et al. | 525/54.1 |

*Primary Examiner*—Thurman K. Page
*Assistant Examiner*—Peter F. Kulkosky
*Attorney, Agent, or Firm*—Sughrue, Mion, Zinn, Macpeak & Seas

[57] ABSTRACT

A water-insoluble functional organic thin film comprising a binder selected from the group consisting of a high molecular weight organic compound and a lipid, having contained therein a biologically active protein and a polymer containing at least one functional group which forms covalent bonds with said biologically active protein.

15 Claims, No Drawings

FUNCTIONAL ORGANIC THIN FILM CHEMICALLY BONDED TO BIOLOGICALLY ACTIVE AGENT

FIELD OF THE INVENTION

This invention relates to a functional organic thin film which contains, as a functional molecule and a biologically active protein, such as an enzyme, antigen, antibody or the like, in a binder matrix. More particularly, this invention relates to a functional organic thin film having a specific interaction with a substrate, which can be used as a thin film detector for sensor use, a separating film and so on.

BACKGROUND OF THE INVENTION

It has been desirable to develop materials suitable for forming water-insoluble organic thin films which can fix biologically active proteins inside the materials thereof for use as biosensors, such as enzyme electrodes. There are only a few types of organic thin films utilized to date. For example, those prepared by dispersing a biologically active protein into resin materials and hardening the resin materials through optical exposure in the presence of a light-sensitive cross-linking agent, e.g., as disclosed in JP-A-62-237348, JP-A-62-238453, JP-A-62-50656, JP-A-61-153559 and EP 0214805 (The term "JP-A" as used herein means an "unexamined published Japanese patent application"). In these films, water-soluble polymers, such as polyvinyl alcohol, polyvinyl pyrrolidone and the like, are used as the resin materials. The cross-linking agents used are dichromic acid, diazo compounds, diazide compounds and so on. The hardening is effected by cross-linking under irradiation with ultraviolet rays.

Additionally, there are films prepared by mixing bioprotein, such as albumin, or a resin material with a biologically active protein, and making the mixture into a film through cross-linking in the presence of a dialdehyde such as gluteraldehyde. Such a film forming method has been widely used because of its simplicity, and instances of enzyme sensors prepared utilizing this method are cited in JP-A-62-23554, JP-A-56-88794, JP-A-62-240849, WO 8607632, EP 0230472 and so on.

Organic thin films formed by the above-described methods are moderately sturdy. In the former case, however, it is feared that the irradiation with light, such as ultraviolet rays, tends to inactivate the biologically active proteins, particularly antibodies. In the latter case, glutaraldehyde is a strong reacting agent and reacts directly with the biologically active protein molecules themselves so as to cross-link them. Thus, the biologically active protein itself is deactivated in part by the film formation and this tends to cause a drop in operability of the sensor or the like.

Also, films disclosed, e.g., in JP-A-61-231454 and JP-A-62-183882 have similar problems because of the analogous hardening means taken therein.

In addition, a method of forming films by covalently bonding succimidyl acrylate to enzyme molecules, in advance, and copolymerizing the reactive monomer obtained and other monomers in the presence of an initiator is disclosed in *Analytical Chemistry*, vol. 57, p. 1920 (1985). However, in analogy with the above-cited instances, there is a fear that the polymerization reaction tends to inactivate the active protein because the polymerization is carried out in the presence of the biologically active protein.

As a result, it has been desired to improve the sensitivity of a biosensor by developing organic thin films, other than the above-described ones, and preparation methods thereof, which are not only excellent in film formability and strength, but also almost free from inactivation of biologically active protein.

SUMMARY OF THE INVENTION

Therefore, an object of this invention is to provide a functional organic thin film which contains biologically active protein and utilizes a novel hardening agent in film formation so as to acquire excellent film formability and to ensure almost undiminished operability of the biologically active protein.

Another object of this invention is to provide a functional organic thin film which is physically stable in that these is no delamination and which maintains high sensing operability when used for an organic thin film sensor, such as a biosensor.

The other objects and effects of this invention will be apparent from the following description.

The above objects of this invention are attained by a water-insoluble functional organic thin film comprising a binder selected from the group consisting of a high molecular weight organic compound and a lipid, having contained therein a biologically active protein and a polymer containing at least one functional group which forms covalent bonds with said biologically active protein.

DETAILED DESCRIPTION OF THE INVENTION

The binders to be used in forming the thin film of this invention are non-crystalline high boiling organic substances, which are useful for forming films on solid substrates.

These organic substances can be classified into the following categories.

1. Natural protein gelatin, casein, albumin, collagen, keratin, silk fibrin, etc.
2. Polysaccharide cellulose and derivatives thereof, chitin, agarose, pullulan, dextran, etc.
3. Japanese lacquer
4. Natural rubber
5. Synthetic polymers polyvinyl alcohol, polyvinyl pyrrolidone, polymethylmethacrylate, polycarbonate, polythiramine, polypyrrole, polyalkyl oxide, polysulfone, etc.
6. Lipid lecithin, cephalin, phosphatidyl choline derivatives, phosphatidyl cephaline derivatives, long-chain alkylated amines, long-chain alkylated ammoniums, fatty acids, fatty acid esters, longchain alkylated amino acids, etc.

Preferred examples of these binders includes hydrophilic colloids, hydrophilic polymers and mixtures thereof, particularly gelatin, albumin and polyvinyl alcohol. These colloids and polymers can be effectively utilized as binders of thin films for sensors because of their high permeabilities to water-soluble compounds.

Gelatin includes the so-called alkali processed gelatin which has been treated with lime or the like in the process of derivation from collagen; the so-called acid processed gelatin which has been treated with hydrochloric acid or the like in the same process as described above; the so-called enzyme processed gelatin which has been treated with hydrolase or the like; and so-called gelatin derivatives or modified gelatins obtained by reforming a functional group contained in a gelatin molecule, such as an amido, imino, hydroxyl or carboxyl group, by treatment with a reagent containing one group capable of reacting with the foregoing functional groups. Specific examples include phthaloylated gelatin, succinated gelatin, trimellitated gelatin and so on. All of these gelatins can be used as the binder. Also, gelatin having a specific molecular weight distribution as disclosed in JP-A-60-80838 can be employed.

In addition, gelatin containing various natural polymers can be used. Typical examples of such natural polymers include the above-cited polysaccharides and natural rubber.

As for the polysaccharides, though many compounds can be used, dextran, pullulan, gum arabic, araban, arabogalactan, galactan and starch are representative thereof.

In addition to these compounds, those disclosed, e.g., in JP-B-35-11989, JP-B-42-16562, JP-B-40-14905 (The term "JP-B" as used herein means an "examined Japanese patent publication"), U.S. Pat. Nos. 3.063,838, 3,137,575, 3,185,569 and 3,152,906, and British Patents 897,497, 992,179, 978,880, 1,071,674, 1,073,625, 976,395, 1,064,215 and 1,063,841 are also useful.

As for the synthetic polymers, those represented by general formula (V-I) are preferred.

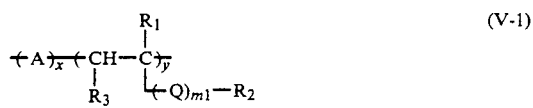
(V-1)

In formula (V-1), A represents a monomer unit obtained by copolymerizing ethylenically unsaturated copolymerizable monomers.

Specific examples of ethylenically unsaturated monomers in formula (V-I) include styrene, hydroxymethylstyrene, sodium vinylbenzenesulfonate, N,N,N-trimethyl-N-vinylbenzylammonium chloride, α-methylstyrene, 4-vinylpyridine, N-vinylpyrrolidone, monoethylenically unsaturated esters of aliphatic acids (e.g., vinyl acetate), ethylenically unsaturated mono- or di-carboxylic acids and the salts thereof (e.g., acrylic acid, methacrylic acid), maleic anhydride, ethylenically unsaturated mono- or di-carboxylic acid esters (e.g., n-butylacrylate, N,N-diethylaminoethylmethacrylate, N,N-diethyl-N-methyl-N-methacryloyloxyethylammonium p-toluenesulfonate), and ethylenically unsaturated mono- or dicarboxylic acid amides (e.g., acrylamide, sodium 2-acrylamido-2-methylpropanesulfonate, N,N-dimethyl-N'-methacryloylpropane-diamineacetate betaine).

$R_1$ in formula (V-1) represents a hydrogen atom, an alkyl group containing 1 to 6 carbon atoms or a halogen atom.

Q in formula (V-1) is a divalent linkage group represented by —O—, —COO—, —CON($R_4$)—, or an arylene group containing 6 to 10 carbon atoms.

$R_2$ in formula (V-1) represents —OH, —COOX, —SO$_3$X (wherein X represents a hydrogen atom, an alkali metal, or an alkaline earth metal),

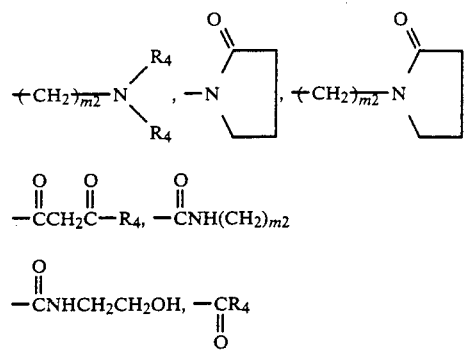

wherein $R_4$ represents a hydrogen atom, or an alkyl group containing 1 to 6 carbon atoms; and $m_2$ represents an integer from 1 to 4.

$R_3$ in formula (V-1) represents —H or —COOX, and X has the same meaning as defined in regard to $R_2$.

x and y in formula (V-1) are monomer fractions expressed in mole %, wherein x ranges from 0 to 99 and y ranges from 1 to 100. $m_1$ represents 0 or 1.

Typical examples of linear polymers represented by formula (V-I), which can be used as the binder of this invention are illustrated below. The polymerization ratios are indicated in terms by mole.

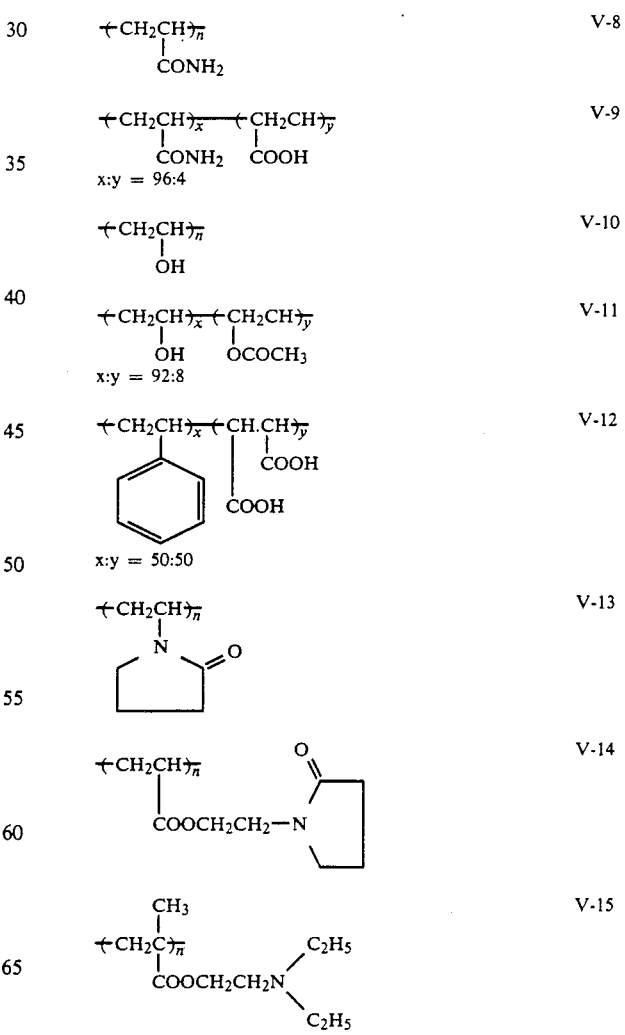

 V-16

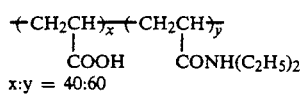 V-17 x:y = 40:60

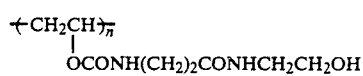 V-18

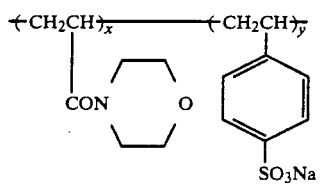 V-19 x:y = 60:40

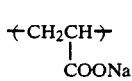 V-20

In addition to these polymers, compounds disclosed in JP-A-49-135619, JP-A-51-14022, JP-A-54-1621, U.S. Pat. Nos. 3,019,104, 3,003,874, 3,043,698, 3,165,412, 3,178,296, 3,271,158, 3,312,553, 3,173,790 and 3,316,097, and British Patents 867,899, 904,863, 861,985, 933,494, 1,010,917, 1,013,905, 976,22, 1,073,238, 1,048,016, 1,069,944, 1,078,335, 1,078,335, 1,076,378, 1,030,001 and 1,053,043 are useful.

Further, the block polymers illustrated below are also useful. The polymerization ratios are indicated in terms by mole.

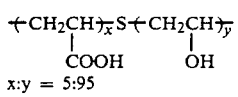 V-21 x:y = 5:95

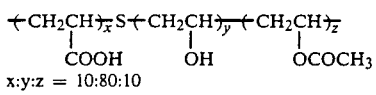 V-22 x:y:z = 10:80:10

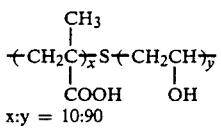 V-23 x:y = 10:90

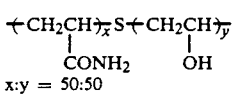 V-24 x:y = 50:50

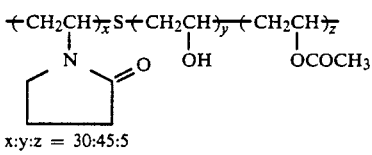 V-25 x:y:z = 30:45:5

The synthetic polymers which can be used as the binder of this invention preferably have a molecular weight of from 2,000 to 2,000,000.

The compounds of this invention, which contain reactive functional groups useful for film formation, are polymer hardening agents. More specifically, it is a polymer containing at least one functional group which forms covalent bonds upon reaction with the biologically active protein.

The above-described polymeric hardening agent of this invention is described in detail below by citing instances.

Among the functional groups capable of reacting with the biologically active protein to be contained in the polymer of this invention, those represented by formulae (1) to (3) are particularly preferred because of their high reactivity.

Other functional groups represented by the formulae (4) to (9) are also useful in this invention.

$$-SO_2CH=CH_2 \quad (1)$$

$$-SO_2CH_2=CH_2X \quad (2)$$

wherein X represents a group which is eliminated through a substitution reaction or an elimination reaction when the functional group of formula (2) is allowed to react with a nucleophilic agent or a base. Specific examples of X include $-Cl$, $-OSO_2CH_3$, $-OSO_2C_6H_4CH_3$, $-OCOCH_3$, $-OSO_3^{\ominus}$,

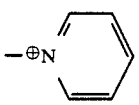

and the like.

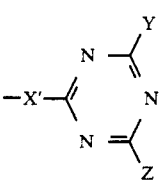 (3)

wherein X' represents a single bond,

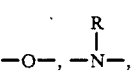

wherein R represents a hydrogen atom, an alkyl group or an aralkyl group; and Y and Z, which may be the same or different, each represents a halogen atom (e.g., Cl, Br), an alkoxy group (e.g., methoxy), a hydroxyl group or a salt thereof, or a substituted or unsubstituted amino group, provided that at least one of Y and Z represents a halogen atom.

$$-CHO \quad (4)$$

 (5)

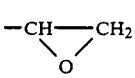

$$-NCO \quad (6)$$

 (7)

 (8)

wherein X″ has the same meaning as X in the formula (2)

  (9)

wherein X''' represents a group capable of easily splitting off when the functional group of formula (9) is allowed to react with an amino group (e.g., Cl,

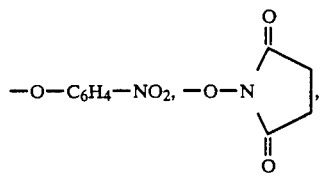

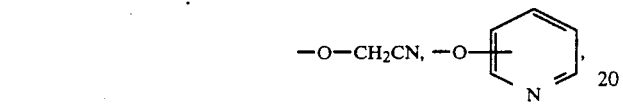

which is generally known as an active ester group or a mixed acid anhydride residue.

This invention is not particularly limited as to the polymerization process to be employed in producing the polymers to be used. For instance, the polymers may be produced using a polycondensation process, or submitting an ethylenically unsaturated bond-containing compound to a radical polymerization process or an anion polymerization process. Further, they may be produced by introducing the foregoing functional groups into natural high molecular compounds.

Also, this invention does not have any particular restriction as to the introduction method of the functional groups capable of reacting with the biologically active protein to be contained in the polymers to be used (e.g., groups represented by the formulae (1) to (9), and hereinafter called "reactive functional groups"). That is, monomers having the reactive functional groups may be employed and submitted to a polymerization reaction, or the foregoing reactive functional groups may be introduced through the so-called macromolecular reaction after the polymers are prepared. In addition, a method which involves polymerizing a monomer containing a precursor of the reactive functional groups, and producing the reactive functional groups from the precursor through an appropriate process is also effective.

The polymeric hardening agent to be used in the present invention is preferably produced by polymerizing the monomer(s), which contain the foregoing reactive functional groups (or a precursor thereof) and an ethylenically unsaturated bond in a molecule, through a radical polymerization process. Representatives of the reactive functional group-containing monomers are illustrated below.

Monomer-1
CH$_2$=CH
   |
   CONHCH$_2$NHCOCH$_2$CH$_2$SO$_2$CH=CH$_2$

Monomer-2
CH$_2$=CH
   |
   CONHCH$_2$NHCOCH$_2$SO$_2$CH=CH$_2$

Monomer-3
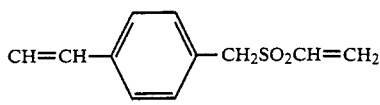

Monomer-4
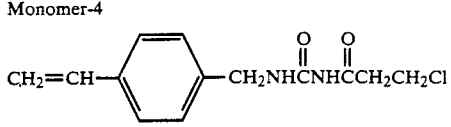

Monomer-5
CH$_2$=CH
   |
   CONHCH$_2$NHCOCH$_2$CH$_2$SO$_2$CH$_2$CH$_2$Cl

Monomer-6
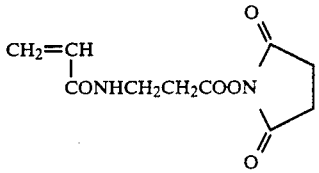

Monomer-7
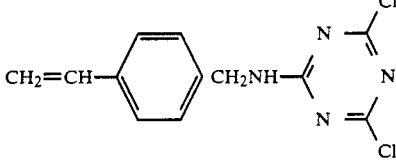

Monomer-8
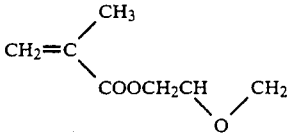

The polymeric hardening agent of this invention may be either homopolymers of the reactive functional group-containing monomers, or copolymers prepared from such monomers and at least one of other monomers. In the case of copolymers, the fraction of the reactive functional group-containing monomers is preferably at least 1 mol %, more preferably not less than 5 mol %. In the copolymerization, any monomers may be used as other monomers so long as they can undergo radical polymerization.

The molecular weight of the polymeric hardening agent of this invention is preferably from 2,000 to 500,000.

Specific examples of such comonomers include aromatic monomers, such as styrene, vinyltoluene, divinylbenzene, N-vinylimidazole, p-vinylbenzoic acid or salts thereof, sodium styrenesulfonate, etc.; ethylenically unsaturated carboxylic acid esters, such as butylacrylate, butylmethacrylate, methylmethacrylate, benzylacrylate, hydroxyethylacrylate, hydroxyethylmethacrylate, N,N-dimethylaminoethylmethacrylate, CH$_2$=CHCOO(CH$_2$CH$_2$O)$_n$R (wherein n is an integer of 1 or more, and R is an alkyl group), etc.; ethylenically unsaturated carboxylic acid amides, such as acrylamide, methacrylamide, N,N-dimethylacrylamide, acryloylmorpholine, etc.; ethylenically unsaturated carboxylic acids, such as acrylic acid, methacrylic acid, etc.; unsaturated nitriles, such as acrylonitrile, methacrylonitrile, etc.; unsaturated chlorine-containing compounds, such as vinyl chloride, vinylidene chloride, etc.; unsaturated fluorinecontaining compounds such as trifluoroethylene, trifluorochloroethylene, etc.; vinyl esters such as vinyl acetate; and other ethylenic unsaturated compounds, e.g., vinyl alcohol, N-vinylpyrrolidone, ethylene and so on.

Typical examples of a polymeric hardening agent to be used in this invention are illustrated below. However, the invention should not be construed as being limited by these examples.

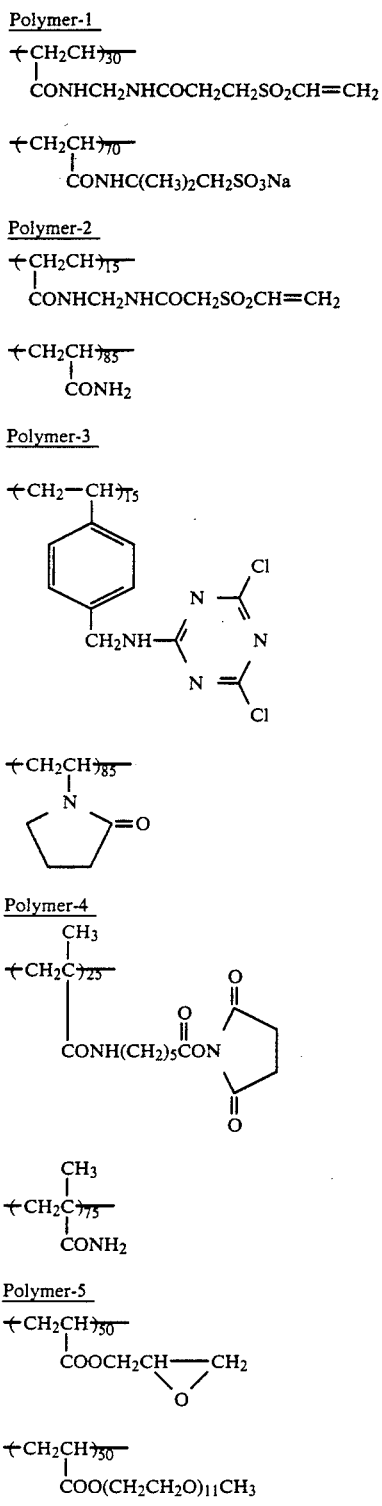

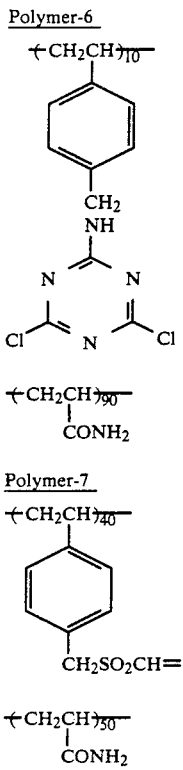

The polymerization ratios are indicated in terms by mole.

The polymer containing at least one functional group capable of reacting with the biologically active protein to form a covalent bond is preferably used in such an amount that the amount of the functional groups is from 1 to 500 mmol (millimole), more preferably from 10 to 100 mmol, per 100 g of the biologically active protein having groups capable of reacting with the foregoing functional groups in the functional organic thin film of this invention.

Biologically active protein to be used in this invention includes biogenic natural substances include enzymes, antigens, and antibodies. Of these substances, enzymes are particularly preferred over others.

Specific examples of enzymes to which this invention is applicable include oxidoreductase, such as glucose oxidase, aminoacid oxidase, catalase, ascorbate oxidase, xanthene oxidase, cholesterol oxidase, glycerol oxidase, glycerol-3-phosphoric acid oxidase, choline oxidase, acethyl-CoA oxidase, aldehyde oxidase, galactose oxidase, sarcosine oxidase, pyruvate oxidase, lactate oxidase, tyrosinase, peroxidase, etc.;

oxidoreduntase, such as uricase, alcohol dehydrogenase, glycerol dehydrogenase, glutamate dehydrogenase, lactate dehydrogenase, malate dehydrogenase, formaldehyde dehydrogenase, 3-α-hydroxysteroid dehydrogenase, cholesterol dehydrogenase, etc.;

transferase, such as creatine kinase, pyruvate kinase, hexokinase, glycerol kinase, myokinase, urokinase, fluctokinase, etc.;

hydrolase, such as urease, asparaginase, amylase, lipase, phospholipase, phosphatase, lactase, aluginase, esterase, trypsin, chymotrypsin, pectinase, penicillinase, etc.;

lyase, such as citrate lyase, decarboxylase, fumarase, aspartase;

isomerase, such as glucose phosphate isomerase, etc.; ligase, such as glutathione synthetase, puruvate synthetase, etc.; and so on.

On the other hand, specific examples of antigens and antibodies include serum albumin, immunoglobulin, syphilis antigen, chorionic gonadotropin, α-fetoprotein, and other various kinds of substances as described in Yuichi Yamamura, Men-eki no Kenkvu (Study of Immunity) published by Dobun Shoin, Japan (1986).

The amount ratio of the binder to the biologically active protein is preferably from $\frac{1}{2}$ to 100 by weight.

The total amount of the functional organic thin film of this invention is preferably from 1 μg to 10 mg, more preferably from 10 μg to 1 mg, per 1 cm$^2$ of the film.

In forming the water-insoluble organic thin film of this invention, various kinds of coating methods for forming a thin film can be employed. For instance, a solution coating method (including a spray coating method, a dip coating method, a spin coating method and so on), a chemical-growth-in-vapor-phase method, a vacuum deposition method, a sputtering method and the like can be used. Of these methods, a solution coating method and a chemical-growth-in-vapor-phase method are preferred over others because precursor compounds contained as the constituents of the thin film can be kept stable. Of solution coating methods, a spin coating method is particularly favored in teams of superiority in uniformity and thinness of the film formed. General methods for thin film formation including a spin coating method and a chemical-growth-in-vapor-phase method, are described in *Hakumaku Handbook* ("Thin Film Handbook") edited by Nippon Gakujutsu Shinkokai in 1983.

Solvents used for the solution coating method are preferably water or a mixture of water and an alcohol. The coating composition for used in the solution coating method can be prepared by dissolving or dispersing the binder, the biologically active protein and the polymeric hardening agent in the solvent. The coating is carried out before completing the reaction between the biologically active protein and the polymeric hardening agent.

In coating a composition for the thin film formation, a dispersant, a stabilizer for preservation, a dye hardener, a thickner and so on can be added to the composition of this invention.

The dry thickness of the organic thin film of this invention is preferably from 50 Å to 10 μm, and more preferably 100 to 5,000 Å.

The functional organic thin film of this invention is preferably provided on a support (substrate).

As for the support used in this invention, a wide variety of materials including conductors such as various metals, vitrified inorganic substances (e.g., glass, quartz) and other inorganic insulators, various inorganic and organic crystals, inorganic semiconductors (e.g., $SnO_2$, $In_2O_3$, ZnO, $TiO_2$, $WO_3$, GaAs, Si), organic semiconductors, organic conductors, organic polymers, and composite materials of two or more of the above-cited substances can be employed. In addition, the support may be an electrode connectable to an outside electric circuit or a transducer, such as a sensor. The support surface can be rendered hydrophilic or hydrophobic through various kinds of chemical and/or physical treatments. For instance, a method desirable for hydrophobic treatment comprises making the substrate surface undergo a reaction with an alkylsilane derivative to function as a coupling agent.

The functional organic thin film of this invention can be used not only in the form of a flat film, but also in the form of a spherical film such as walls of microcapsules.

Examples of functional thin films in accordance with this invention are described below in comparison with those obtained by the conventional methods. However, the application of this method should not be construed as being limited to these examples.

COMPARATIVE EXAMPLE 1

An organic thin film containing glucose oxidaze (GOD) as the enzyme was prepared in the following manner.

11 mg of GOD (Grade II, produced by Behringer-Mannheim) was dissolved in 3 cc of a 2 wt % aqueous solution of bovine serum albumin (BSA), and then 62 μl (microliters) of a 4 wt % aqueous solution of glutaraldehyde (corresponding to 25 micromole of glutaraldehyde) as a hardener was added thereto. Water was further added to make the total volume 4 ml. A 100 μl portion of the thus prepared film-forming solution was put on one side of a polyethylene terephthalate film (2×2 cm), uniformly spread out, and dried for 6 hours at 40° C. to form a thin film.

COMPARATIVE EXAMPLE 2

Two 3 ml portions of a 2 wt % aqueous gelatin solution were prepared instead of BSA, and 11 mg of GOD was dissolved into each portion. 62 μl of a 4 wt % aqueous solution of glutaraldehyde (corresponding to 25 micromole of glutaraldehyde) and 249 μl of the 4 wt % aqueous solution of glutaraldehyde (corresponding to 100 micromole of glutaraldehyde) were further added thereto, respectively. Then, the total volume of each solution was made 4 ml by the addition of water. 100 μl samples were withdrawn from the thus prepared two kinds of film-forming solutions, respectively, and uniformly spread on separate polyethylene terephthalate films (2x2 cm). Thereafter, they were dried for 6 hours at 40° C to form gelatin thin films.

EXAMPLE 1

Thin films containing GOD were prepared using BSA or gelatin as a binder in the same manner as in Comparative Examples, except Polymer-1 or Polymer-3, illustrated as compound examples hereinbefore, were used as a hardening agent in place of glutaraldehyde. Each of the thus obtained film-forming solutions was spread on a polyethylene terephthalate film (2×2 cm), dried for 6 hours at 40° C., and then allowed to stand overnight at room temperature to form a thin film. The amounts of the binders used and those of the hardeners used are shown in the Table 1 below.

The operability of the thus prepared various thin films was evaluated by measuring the activity of the GOD. More specifically, each of the thin film-carrying polyethylene terephthalate films was soaked in 4 cc of a phosphate buffer adjusted to pH 6.4 in which 0.01 mole of β-D-glucose, 1.8 mg of peroxidase (POD) and diammonium 2,2'-azino-bis(3-ethylbenzothiazoline-6-sulfonate) (ABTS) as a coloring reagent were contained. The time-course of the absorbance of ABTS coloration coming from the oxidation of glucose was measured at 30° C.

The reactions ar schematically indicated below.

Glucose + O$_2$ $\xrightarrow{\text{GDO}}$ Gluconic acid + H$_2$O$_2$

H$_2$O$_2$ + ABTS $\xrightarrow{\text{POD}}$ H$_2$O + ABTSox wherein ABTSox represents an oxidized ABTS.

The absorbance was monitored at 740 nm in the absorption peak of the oxidized ABTS. In each thin film, the absorbance increased linearly with time. The slopes of these linearly increased absorbances ($\Delta$OD/min.cm) were determined, and adopted as a criterion of the relative activities of GOD.

The results obtained are shown in the Table 1 below.

TABLE 1

Activities of GOD-carrying Organic thin films

| No. | Binder Substance | Binder Amount (mg) | Hardening agent Compound | Hardening agent Amount ($\mu$mol) | Relative activity of GOD ($\Delta$OD/min·cm) |
|---|---|---|---|---|---|
| 1 (Comparison) | BSA | 60 | Glutaraldehyde | 25 | 0.260 |
| 2 (Invention) | BSA | 60 | Polymer-1 | 25 | 0.400 |
| 3 (Comparison) | Gelatin | 60 | Glutaraldehyde | 25 | 0.100 |
| 4 (Invention) | Gelatin | 60 | Polymer-1 | 25 | 0.150 |
| 5 (Invention) | Gelatin | 60 | Polymer-3 | 25 | 0.180 |

The amounts of the binders and the hardening agent were those contained in 4 cc of film-forming solutions. The amounts of GOD added to all samples were the same, i.e., 11 mg/4 cc.

It can be understood from the results in Table 1 that the functional organic thin film of this invention attains high activity of the enzyme compared to the films prepared by the conventional manners.

EXAMPLE 2

On an ion-sensitive field effect transistor (ISFET) containing a silicon nitride film as a gate, an organic thin film containing urease as the enzyme was formed in the following manner to prepare an urea sensor.

To an aqueous solution containing 3 wt % of BSA and 3 wt % of urease, Polymer-3 of this invention was added in an amount of 1 wt % to prepare a film-forming solution. Immediately after the preparation, the tip of an ISFET was dipped in the film-forming solution for 10 seconds at room temperature in order that the gate part might be completely under the solution. Thereafter, it was pulled up into the air, and dried for about 30 minutes. Thus, an enzyme film was formed o the gate part.

The thin film-carrying ISFET was allowed to stand overnight to complete the hardening.

The thus obtained ISFET biosensor was put in a 2 mM neutral phosphate buffer containing urea in an amount of from 0 to 10 mM, and the potential response was measured. As the result, a good linear relationship between the responses and the logarithms of urea concentrations (60 mV/unit log urea concentration) was obtained.

As stated in the foregoing, the present invention provides a functional organic thin film acquiring excellent film formability and ensuring undiminished poerability of the biologically active protein.

While the invention has been described in detail and with reference to specific embodiments thereof, it will be apparent to one skilled in the art that various changes and modifications can be made therein without departing from the spirit and scope thereof.

What is claimed is:

1. A water-insoluble functional organic thin film comprising a binder selected from the group consisting of a high molecular weight organic compound and a lipid, each having a functional group capable of reacting with an —SO$_2$CH=CH$_2$ group, said binder having contained therein a biologically active protein and a polymer, said polymer comprising at least one of the following monomers:

Monomer-1:

CH$_2$=CH
|
CONHCH$_2$NHCOCH$_2$CH$_2$SO$_2$CH=CH$_2$;

Monomer-2:

CH$_2$=CH
|
CONHCH$_2$NHCOCH$_2$SO$_2$CH=CH$_2$; and

Monomer-3:

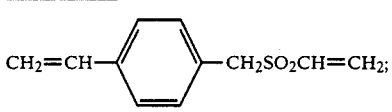

wherein covalent bonds are formed between said polymer and biologically active protein upon hardening of said film.

2. A water-insoluble functional organic thin film as claimed in claim 1, wherein said binder is selected from a hydrophilic colloid, a hydrophilic polymer and a mixture thereof.

3. A water-insoluble functional organic thin film as claimed in claim 2, wherein said binder is gelatin or albumin.

4. A water-insoluble functional organic thin film as claimed in claim 1, wherein said polymer comprises 1 mol % or more of said at least one monomer based on the amount of said polymer.

5. A water-insoluble functional organic thin film as claimed in claim 4, wherein said polymer comprises 5 mol % or more of said at least one monomer based on the amount of said polymer.

6. A water-insoluble functional organic thin film as claimed in claim 1, wherein said polymer is employed in such an amount that the amount of —SO$_2$CH=CH$_2$ groups in the polymer is from 1 to 500 mmol per 100 g of substances having groups capable of reacting with said $-SO_2CH=CH_2$ groups contained in said functional organic thin film.

7. A water-insoluble functional organic thin film as claimed in claim 6, wherein said polymer is employed in such an amount that the amount of said $-SO_2CH=CH_2$ groups is from 10 to 100 mmol per 100 g of substances having groups capable of reacting with said $-SO_2CH=CH_2$ groups contained in said functional organic thin film.

8. A water-insoluble functional organic thin film as claimed in claim 1, wherein said biologically active protein is an enzyme.

9. A water-insoluble functional organic thin film as claimed in claim 1, wherein the molecular weight of said polymer is from 2,000 to 500,000.

10. A water-insoluble functional organic thin film as claimed in claim 1, wherein the amount ratio of said binder to said biologically active protein is from ½ to 100 by weight.

11. A water-insoluble functional organic thin film as claimed in claim 1, wherein the total amount of said water-insoluble functional organic thin film is from 1 $\mu$g to 10 mg per 1 $cm^2$ of said film.

12. A water-insoluble functional organic thin film as claimed in claim 11, wherein the total amount of said water-insoluble functional organic thin film is from 10 $\mu$g to 1 mg, per 1 $cm^2$ of the film.

13. A water-insoluble functional organic thin film as claimed in claim 1, wherein the dry thickness of said water-insoluble functional organic thin film is from 50 Å to 10 $\mu$m.

14. A water-insoluble functional organic thin film as claimed in claim 13, wherein the dry thickness of said water-insoluble functional organic thin film is from 100 to 5,000 Å.

15. A water-insoluble functional organic thin film as claimed in claim 1, wherein said water-insoluble functional organic thin film is provided on a support.

* * * * *